United States Patent
Hayakawa

(10) Patent No.: US 7,597,001 B2
(45) Date of Patent: Oct. 6, 2009

(54) HUMIDITY MEASURING APPARATUS AND IMAGE FORMING APPARATUS

(75) Inventor: Masahiro Hayakawa, Odawara (JP)

(73) Assignee: Canon Kabushiki Kaisha, Tokyo (JP)

( * ) Notice: Subject to any disclaimer, the term of this patent is extended or adjusted under 35 U.S.C. 154(b) by 275 days.

(21) Appl. No.: 11/671,529

(22) Filed: Feb. 6, 2007

(65) Prior Publication Data

US 2007/0186650 A1     Aug. 16, 2007

(30) Foreign Application Priority Data

Feb. 16, 2006    (JP) .............................. 2006-039125

(51) Int. Cl.
    G01N 27/12    (2006.01)
(52) U.S. Cl. ................................. 73/335.05
(58) Field of Classification Search ............... 73/335.05
    See application file for complete search history.

(56) References Cited

U.S. PATENT DOCUMENTS 5,065,625 A     11/1991    Nakagawa et al. ......... 73/336.5
5,381,954 A *   1/1995    Tokizaki ................... 236/78 D
5,585,559 A     12/1996    Hata ........................ 73/335.02
6,029,021 A *   2/2000    Nishimura et al. ............ 399/49
6,173,134 B1 *  1/2001    Nishimura et al. ............ 399/58

FOREIGN PATENT DOCUMENTS

JP            02-298848          12/1990
JP            07-311169          11/1995

\* cited by examiner

*Primary Examiner*—Hezron Williams
*Assistant Examiner*—Rodney T Frank
(74) *Attorney, Agent, or Firm*—Fitzpatrick, Cella, Harper & Scinto

(57) ABSTRACT

A humidity measuring apparatus including: a humidity detecting element whose resistance value changes according to a humidity change; a resistor serially connected to the humidity detecting element; a signal output unit which outputs a clock signal to the humidity detecting element and the resistor; and a measuring unit which detects a voltage of a connecting point of the humidity detecting element and the resistor at predetermined timing from an edge of the clock signal and obtains a humidity based on the detected voltage, wherein an abnormality of the humidity detecting element is detected by detecting the voltage at timing different from the predetermined timing based on the voltage detected by the measuring unit.

10 Claims, 11 Drawing Sheets

HUMIDITY MEASURING APPARATUS AND IMAGE FORMING APPARATUS

BACKGROUND OF THE INVENTION

1. Field of the Invention

The present invention relates to a humidity measuring apparatus suitable for an image forming apparatus such as one of a copying apparatus and a printer using an electrophotographic system and, more particularly, to an error detection of such an apparatus.

2. Description of the Related Art

Generally, in an image forming apparatus of an electrophotographic system, a fluctuation occurs in concentration characteristics of a print image due to a using environment, a characteristics fluctuation of a developing device and a photosensitive drum depending on the number of print copies, a sensitivity variation of the photosensitive drum upon manufacturing, and a variation in frictional charging characteristics upon manufacturing of toner. Although an effort to stabilize those changes and fluctuating characteristics is being made everyday, it is insufficient yet. Particularly, in a color image forming apparatus, since a color image is reproduced by overlaying developers (toner) of four colors of yellow, magenta, cyan, and black, if concentrations of the developers of the four colors, that is, toner images are not accurately adjusted, a good color balance cannot be obtained. Therefore, in many color image forming apparatuses, the using environment is monitored and image forming conditions such as charging potential, exposure amount, and developing bias are changed to optimum values according to the using environment.

In the color image forming apparatus, generally, various humidity sensor elements are used to monitor the using environment. As a humidity sensor element, a humidity sensor element using such a phenomenon that an impedance changes due to an adsorption of water molecular is known. Such impedance change type humidity sensor elements include a ceramics humidity sensor element and a high molecular system sensor element.

The impedance change type humidity sensor element is further classified into an element using a resistance change (R change) and an element using an electrostatic capacitance change (C change).

An electrostatic capacitance of the electrostatic capacitance change type humidity sensor element (high molecular system sensor element) decreases at an almost same ratio according to an increase in humidity. The resistance change type humidity sensor element has a high resistance on the low humidity side and its resistance value exponentially decreases (RH-C characteristics become almost linear) according to the increase in humidity. The electrostatic capacitance change type humidity sensor element (high molecular system sensor element) has an excellent linearity and can measure the humidity from a relative humidity of 0% RH. However, the electrostatic capacitance at 0% RH is large to be hundreds of pF. A change width of the electrostatic capacitance at 0 to 100% RH is small to be tens of pF. Therefore, it is necessary to increase the small capacitance change and, at the same time, set off a large zero offset. There are, consequently, such problems that a circuit becomes very complicated, costs are high, and a periodic calibration is necessary.

According to the resistance change type humidity sensor element, since it is difficult to measure a low humidity area (5% RH or less) and a change width of the impedance shows exponential function characteristics of four to five digits, there is such a problem that it is difficult to assure a dynamic range of a circuit system. Further, there is such a problem that the characteristics fluctuation by a temperature is large. However, since such problems can be solved by devising the circuit system and additionally using a temperature detecting element, the resistance change type humidity sensor element is used in the invention. Circuit constructional diagrams for detecting the humidity have been proposed in Japanese Patent Application Laid-Open No. H02-298848 or Japanese Patent Application Laid-Open No. H07-311169.

According to Japanese Patent Application Laid-Open No. H02-298848 or Japanese Patent Application Laid-Open No. H07-311169, the circuit construction is devised so as to obtain good linearity characteristics in the whole humidity area in a range from the low humidity side to the high humidity side. However, since the circuit construction proposed in one of Japanese Patent Application Laid-Open No. 2-298848 and Japanese Patent Application Laid-Open No. H077-311169 is expensive, it is necessary to detect the humidity by a more reasonable circuit construction.

FIG. 1 (although it is a diagram of an embodiment, it is also cited in common to describe the related art) is a diagram illustrating a general circuit construction of a humidity detecting circuit for detecting the humidity by using an impedance change. In the diagram, a power source (for example, +3.3V) is supplied to a microprocessor mounted on a board. A signal of a predetermined frequency (for example, 1 kHz), an amplitude (for example, +3.3V), and a duty ratio (for example, 50%) is output from the microprocessor. An output signal CLK and an output signal /CLK whose polarity is opposite to the polarity of the signal CLK are supplied to a humidity sensor element 101 through a voltage dividing resistor 102. A value of the voltage division with the resistor 102 is input to the microprocessor.

FIG. 15 is a diagram illustrating a signal waveform of each section in FIG. 1. The CLK signal and the /CLK signal are output from the microprocessor. A sensor signal SNS is A/D-input. Timing for the A/D input is detected after the elapse of a specified time while setting a leading edge of the CLK signal to a reference. The humidity is calculated from a detection voltage of the sensor signal SNS by using a detection voltage-humidity conversion table.

However, the above related arts have the following problems.

FIG. 16 illustrates signal waveforms at the time of the high humidity and the low humidity when using the circuit illustrated in FIG. 1. In the related arts, since the impedance change width of the humidity sensor element 101 in the range from the low humidity side to the high humidity side shows the exponential function characteristics, a dynamic range of a detection voltage Vi (refer to FIG. 16) is wide. That is, in the signal waveforms at the time of the high humidity and the low humidity, a fluctuation in the voltage which is detected depending on the humidity change is small. For example, when the humidity sensor element fails due to a disconnection or the like, a detection voltage value is the same as the value at the time of one of the high humidity and the low humidity and does not fluctuate. Therefore, at the time of one of the high humidity and the low humidity, it is difficult to detect from the A/D input value of the sensor signal SNS whether a cause of the failure is based on an abnormality of the humidity sensor element 101 or based on one of the high humidity and the low humidity. That is, the abnormality of the humidity sensor element 101 cannot be accurately detected. Thus, even when the humidity sensor element 101 is abnormal, the cause is determined to be based on one of the high humidity and the low humidity, the using humidity is erroneously detected, and abnormal values are set into the image forming conditions such as charging potential, and exposure amount, developing bias.

The invention is made under such circumstances and it is an object of the invention to provide an image forming apparatus which detects an error of a humidity measuring apparatus by a reasonable construction and can continuously provide images of high quality.

SUMMARY OF THE INVENTION

It is an object of the invention to provide a humidity measuring apparatus comprising: a humidity detecting element whose resistance value changes according to a humidity change; a resistor serially connected to the humidity detecting element; a signal output unit which outputs a clock signal to the humidity detecting element and the resistor; and a measuring unit which detects a voltage of a connecting point of the humidity detecting element and the resistor at predetermined timing from one of a leading edge and a trailing edge of the clock signal and obtains a humidity based on the detected voltage, wherein an abnormality of the humidity detecting element is detected by detecting the voltage at timing different from the predetermined timing based on the voltage detected by the measuring unit.

Another object of the invention to provide an image forming apparatus comprising: an image forming unit which forms an image; a humidity detecting apparatus having a humidity detecting element whose resistance value changes according to a humidity change and a resistor serially connected to the humidity detecting element; a signal output unit which outputs a clock signal to the humidity detecting element and the resistor; a measuring unit which detects a voltage of a connecting point of the humidity detecting element and the resistor at predetermined timing from one of a leading edge and a trailing edge of the clock signal and obtains a humidity based on the detected voltage; and a control unit which controls the image forming unit, wherein the control unit detects an abnormality of the humidity detecting element by detecting the voltage at timing different from the predetermined timing based on the voltage detected by the measuring unit.

Further features of the present invention will become apparent from the following description of exemplary embodiments with reference to the attached drawings.

DESCRIPTION OF THE EMBODIMENTS

Exemplary embodiments for embodying the invention will be described in detail hereinbelow by embodiments.

Embodiment 1

Figure 1:
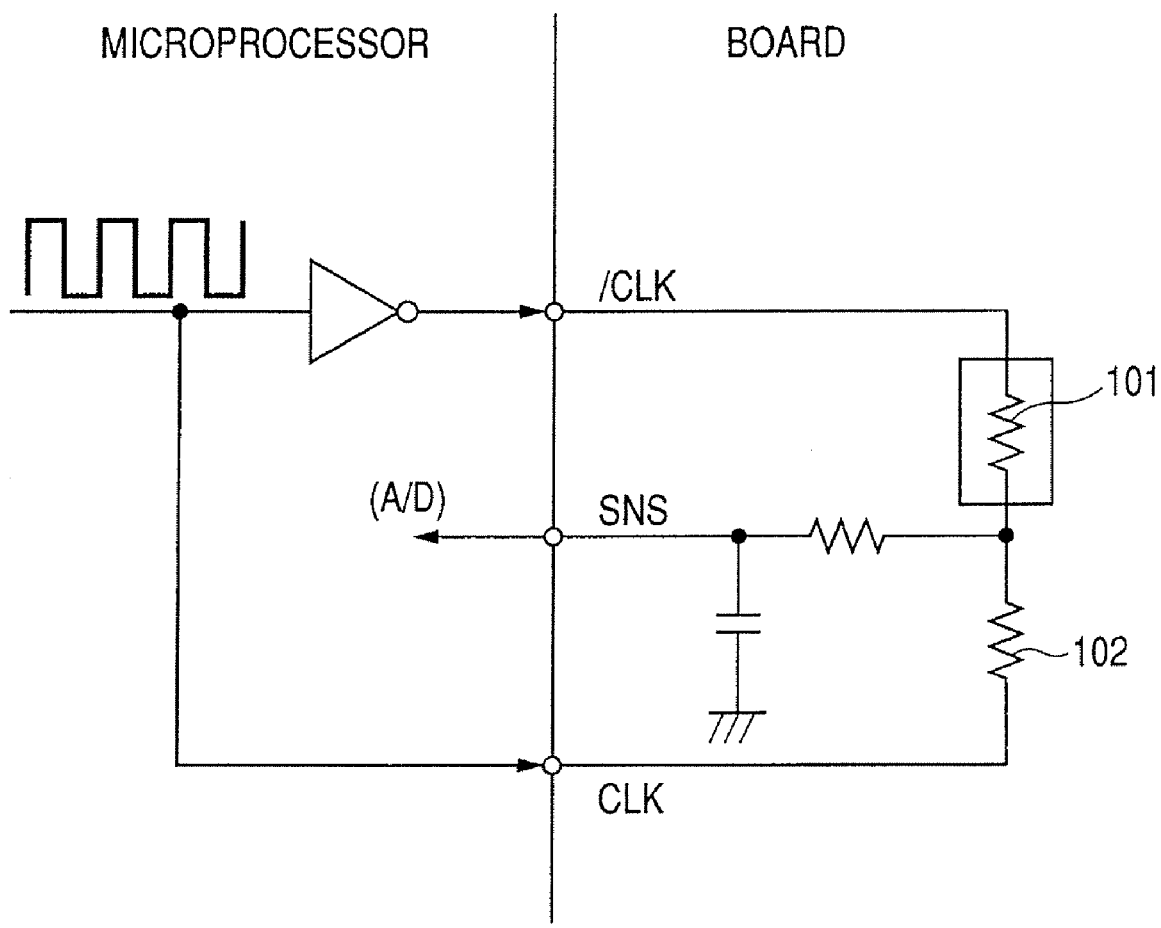
FIG. 1 is a diagram illustrating a construction of a humidity detecting circuit used in an embodiment 1.
Figure 2:
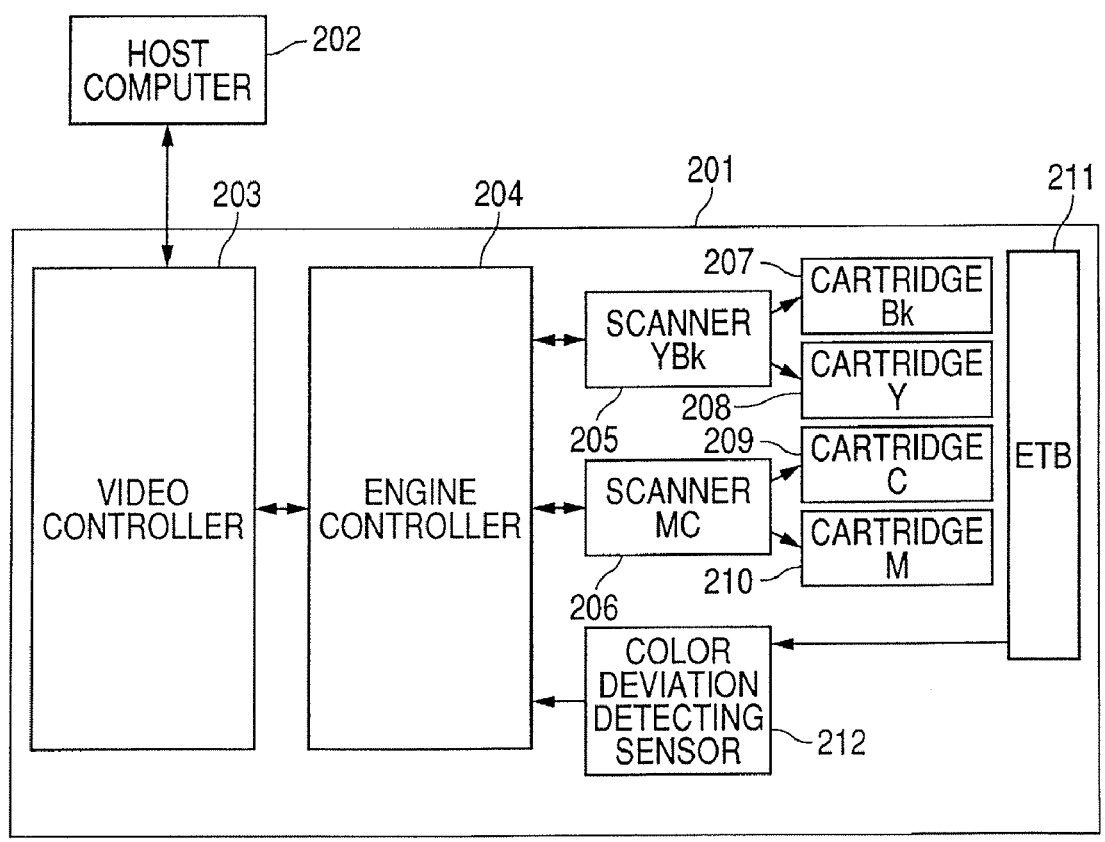
FIG. 2 is a block diagram illustrating a construction of the embodiment 1.

A color laser printer and a humidity detecting circuit which is used in the color laser printer according to the embodiment will now be described. In the embodiment, an error detection under a high humidity environment will be described. FIG. 1 is a diagram illustrating a construction of a humidity detecting circuit used in the embodiment. FIG. 2 is a block diagram illustrating a construction of the embodiment. A laser printer 201 and a host computer 202 are provided. In the embodiment, a 4-drum type color laser printer will be described.

Figure 3:
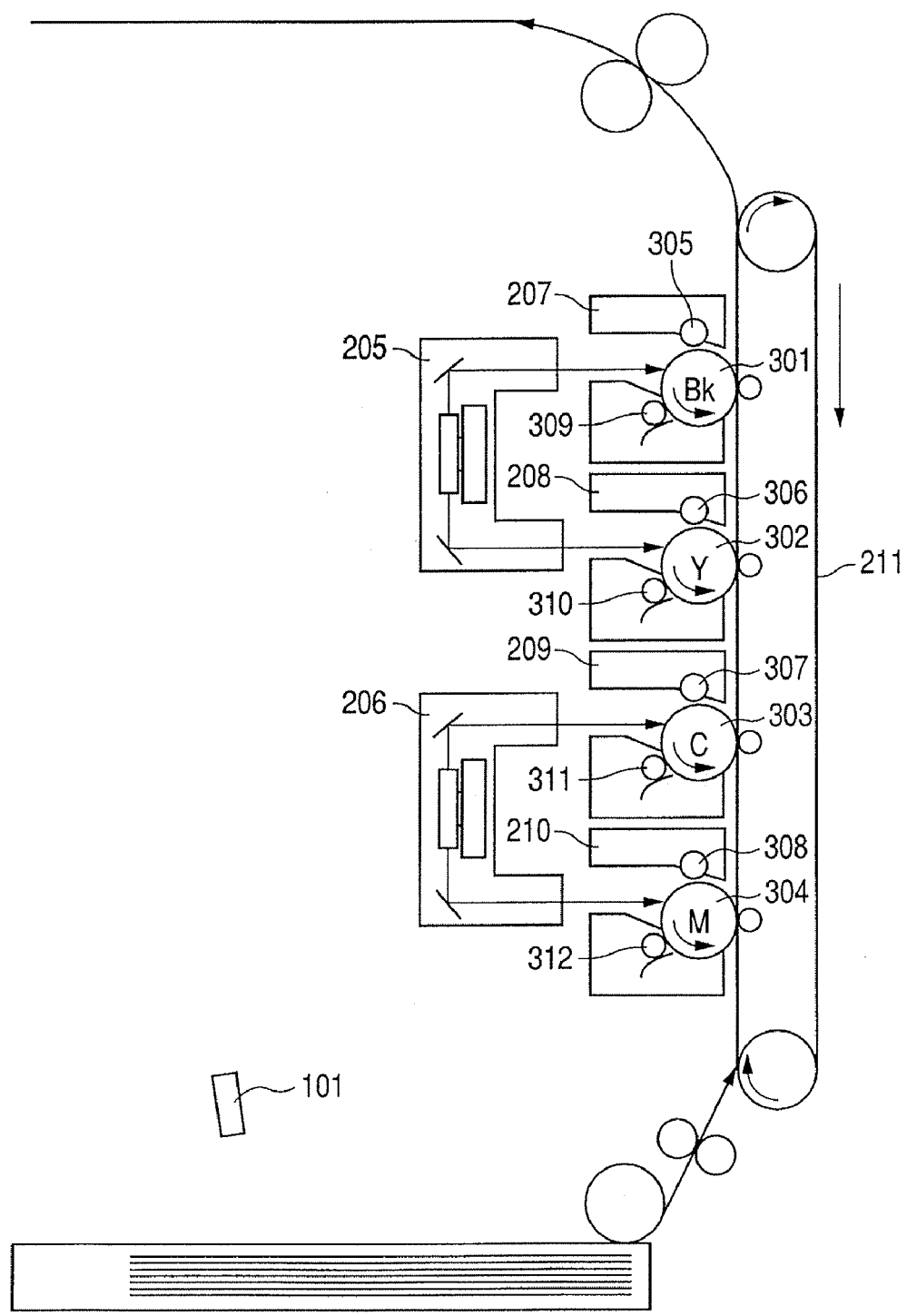
FIG. 3 is a cross sectional view illustrating a structure of the embodiment 1.

FIG. 3 is a cross sectional view illustrating a structure of the color laser printer of the embodiment. The same component elements as those in FIG. 2 are designated by the same reference numerals. A video controller and an engine controller illustrated in FIG. 2 are not illustrated in FIG. 3. Photosensitive drums 301 to 304 are provided. The photosensitive drum 301 is used to form a black image. The photosensitive drum 302 is used to form a yellow image. The photosensitive drum 303 is used to form a cyan image. The photosensitive drum 304 is used to form a magenta image. The photosensitive drum 301 is rotated at a predetermined speed by a drum motor (not illustrated) in the direction shown by an arrow in FIG. 3.

The surface of the black photosensitive drum 301 has uniformly been charged by a charging roller 309 in FIG. 3. This surface is scanned by a laser beam modulated by a video signal formed by a video controller 203, so that an electrostatic latent image is formed. The electrostatic latent image is visualized as a toner image by a developing device 305 in FIG. 3. This is true of yellow, cyan, and magenta.

The color laser printer has image forming units of four colors (yellow Y, magenta M, cyan C, and black BK) in order to form a color image obtained by overlaying images of the four colors. The image forming units include: toner cartridges 207 to 210 each having a photosensitive drum as an image bearing member; and scanner units 205 and 206 each having a laser diode as an image exposing light source for emitting a laser beam. Among them, the toner cartridge is provided for each of the four colors. However, the scanner unit 206 is used in common for cyan and magenta and the scanner unit 205 is used in common for yellow and black.

When image data is received from the host computer 202, the video controller 203 in the laser printer 201 develops the image data into bit map data and forms a video signal to form the image. The video controller 203 and an engine controller 204 serially communicate with each other, thereby transmitting and receiving information. The video signal is transmitted to the engine controller 204. The engine controller 204 drives laser diodes (not illustrated) in the scanner units 205 and 206 according to the video signal and forms images onto the photosensitive drums (not illustrated) in the toner cartridges 207 to 210, respectively. The photosensitive drums 301 to 304 are in contact with an ETB (Electrostatic Transportation Belt) 211. The images formed on the photosensitive drums of the colors are sequentially transported and overlaid onto a recording sheet on the ETB 211, so that a color image is formed.

The humidity is monitored by the humidity sensor element 101 (refer to FIG. 1). Image forming conditions such as charging potential, exposure amount, and developing bias are set to optimum values according to the using environment.

Figure 4:
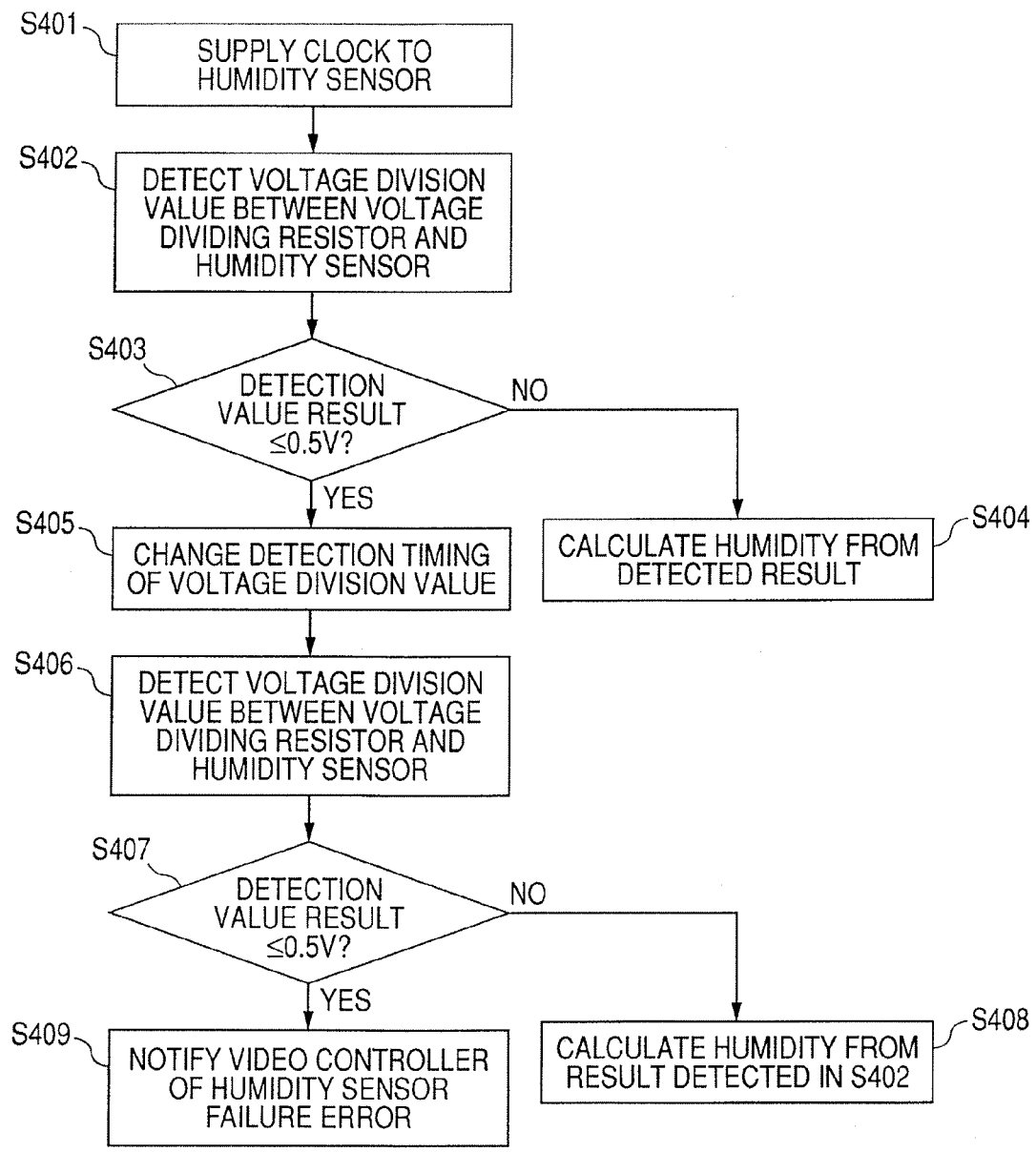
FIG. 4 is a flowchart showing processes of the embodiment 1.
Figure 5:
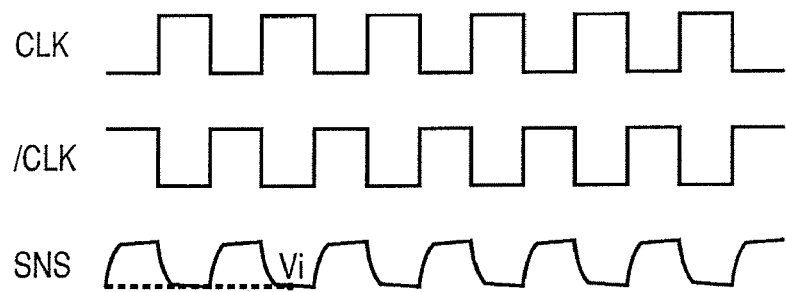
FIG. 5 is a waveform diagram of a humidity detecting circuit.

A flow of error detection under the high humidity environment will now be described with reference to a flowchart of FIG. 4. In the flowchart, each processing step is abbreviated as "S" and the humidity sensor element is abbreviated as "humidity sensor". A clock signal of a frequency (1 kHz), an amplitude (+3.3V), and a duty ratio (50%) is output from the microprocessor in FIG. 1 (S401). The output clock signal CLK and the signal SNS from the humidity detecting circuit are shown in FIG. 5. The output clock signal CLK and the output signal /CLK whose polarity is opposite to the polarity of the signal CLK are supplied to the humidity sensor element 101 through the voltage dividing resistor 102. The value Vi of the voltage division (refer to FIG. 5) with the resistor 102 after the elapse of 250 μsec from the leading edge of the output clock signal CLK is input to the microprocessor (S402) Whether or not a detection result in S402 is equal to or less than 0.5V is discriminated (S403).

Figure 6:
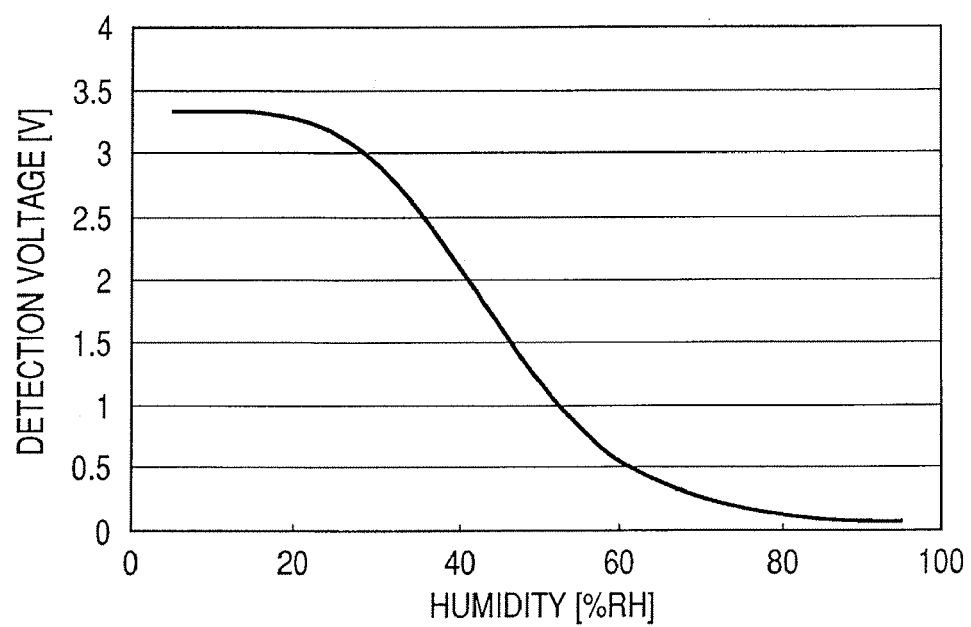
FIG. 6 is a table showing a correlation between an output of the humidity detecting circuit and a humidity.

FIG. 6 is a table showing a correlation between a voltage division value as a signal from the humidity detecting circuit and a humidity. When the voltage exceeds 0.5V, the humidity is calculated from the detection result by using the detection voltage–humidity conversion table shown in FIG. 6 (S404). When the voltage is equal to or less than 0.5V, it is determined that the humidity is high or the humidity sensor element has failed. The apparatus is shifted to a failure discriminating mode.

The reason why the apparatus is shifted to the failure discriminating mode when the voltage is equal to or less than 0.5V is as follows.

Figure 16:
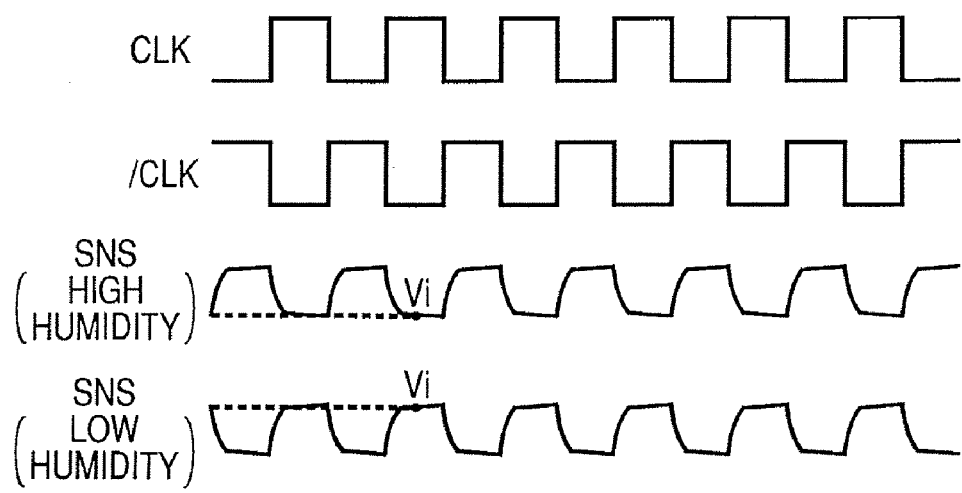
FIG. 16 is a waveform diagram of the humidity detecting circuit.

According to the humidity detecting circuit of the embodiment, in the case of the high humidity of 80% or more, a change amount of the detection voltage to a humidity change is small (refer to FIG. 16). Therefore, it is difficult to discriminate the state where the humidity detecting element fails and outputs a predetermined voltage value of 0.5V or less and the state of the high humidity. The apparatus is shifted to the failure discriminating mode in order to discriminate whether or not the humidity sensor element has failed.

Figure 7:
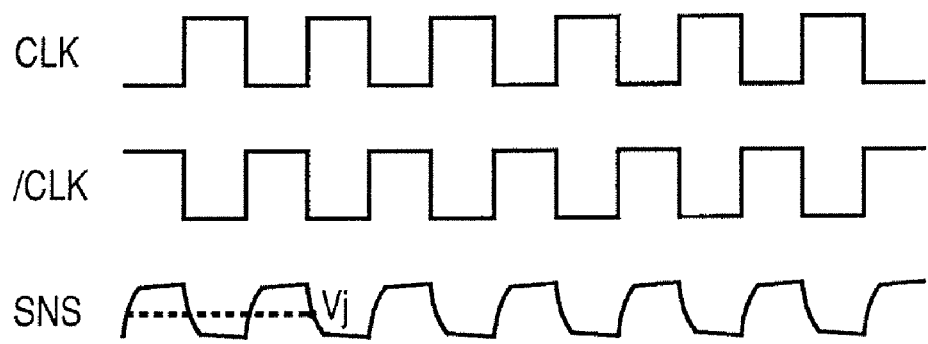
FIG. 7 is a waveform diagram of the humidity detecting circuit.

In the failure discriminating mode, detection timing for inputting the voltage division value to the microprocessor is changed from the timing after the elapse of 250 μsec from the leading edge of the clock signal CLK to the timing after the elapse of 50 μsec (S405). The output clock signal and the signal from the humidity detecting circuit are shown in FIG. 7. The output clock signal CLK and the output signal /CLK whose polarity is opposite to the polarity of the output clock signal CLK are supplied to the humidity sensor element 101 through the voltage dividing resistor 102. A value Vj of the voltage division (refer to FIG. 7) with the resistor 102 is input to the microprocessor (S406). Whether or not a detection result in S406 indicates that the voltage division value Vj is equal to or less than 0.5V is discriminated (S407). If it exceeds 0.5V, the humidity is calculated by using the detection voltage–humidity conversion table shown in FIG. 6 from the voltage division value Vi which has already been detected (S408). When it is equal to or less than 0.5V, the engine controller 204 notifies the video controller 203 of an error indicative of the failure of the humidity sensor element (S409).

An example of specific numerical values of the embodiment (when the humidity sensor element 101 is not abnormal) is shown below. The clock signal of the frequency (1 kHz), the amplitude (+3.3V), and the duty ratio (50%) is output from the microprocessor in FIG. 1. The output signal CLK and the output signal /CLK whose polarity is opposite to the polarity of the output signal are supplied to the humidity sensor element 101 through the voltage dividing resistor 102. The value of the voltage division with the voltage division resistance of 68 kΩ (refer to 102 in FIG. 1) is input to the microprocessor. When the detection voltage is equal to 0.1V, the apparatus is shifted to the failure discriminating mode. In the failure discriminating mode, the detection timing for inputting the voltage division value to the microprocessor is changed from the timing after the elapse of 250 μsec from the leading edge of the clock signal CLK to the timing after the elapse of 50 μsec. The output signal and the output signal whose polarity is opposite to the polarity of the output signal are supplied to the humidity sensor element 101 through the voltage dividing resistor 102. The value of the voltage division with the voltage division resistance of 68 kΩ is input to the microprocessor. When the detection voltage is equal to, for example, 1.2V, that is, when the detection voltage is not equal to a predetermined voltage value of 0.5V or less, it is determined that the humidity sensor element does not failed. The humidity at the detection voltage of 0.1V is calculated by using the detection voltage–humidity conversion table (refer to FIG. 6) and the humidity is detected to be 84% RH.

Figure 8:
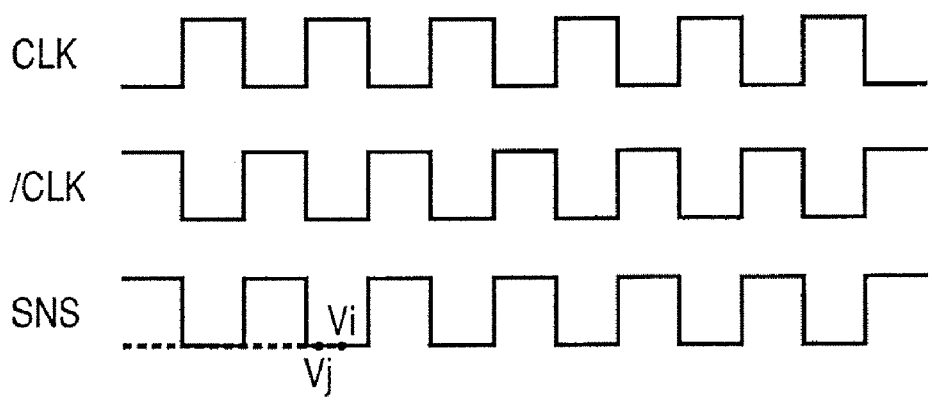
FIG. 8 is a waveform diagram of the humidity detecting circuit.

An example of specific numerical values of the embodiment (when the humidity sensor element 101 is abnormal) is shown below. FIG. 8 shows the output clock signal in the embodiment and the signal from the humidity detecting circuit. The clock signal of the frequency (1 kHz), the amplitude (+3.3V), and the duty ratio (50%) is output from the microprocessor in FIG. 1. The output signal CLK and the output signal /CLK whose polarity is opposite to the polarity of the output signal are supplied to the humidity sensor element 101 through the voltage dividing resistor 102. The value of the voltage division with the voltage division resistance of 68 kΩ (refer to 102 in FIG. 1) is input to the microprocessor. When the detection voltage is equal to 0.1V, the apparatus is shifted to the failure discriminating mode. In the failure discriminating mode, the detection timing for inputting the voltage division value to the microprocessor is changed from the timing after the elapse of 250 μsec from the leading edge of the clock signal CLK to the timing after the elapse of 50 μsec. The output signal and the output signal whose polarity is opposite to the polarity of the output signal are supplied to the humidity sensor element 101 through the voltage dividing resistor 102. The value of the voltage division with the voltage division resistance of 68 kΩ is input to the microprocessor. When the detection voltage is equal to, for example, 0.1V, it is determined that the humidity sensor element has failed. The video controller 203 is notified of the error showing the failure of the humidity sensor element.

As described above, according to the embodiment, since the abnormality of the humidity sensor element can be discriminated by the reasonable circuit construction, the images of the high quality can be continuously provided by setting the image forming conditions according to the output of the humidity sensor element.

Embodiment 2

A humidity detecting circuit in the embodiment 2 will now be described. This embodiment relates to an error detection on the low humidity side. Since a construction of hardware is similar to that of the embodiment 1, its explanation is also cited in common and a specific description is omitted here.

Figure 9:
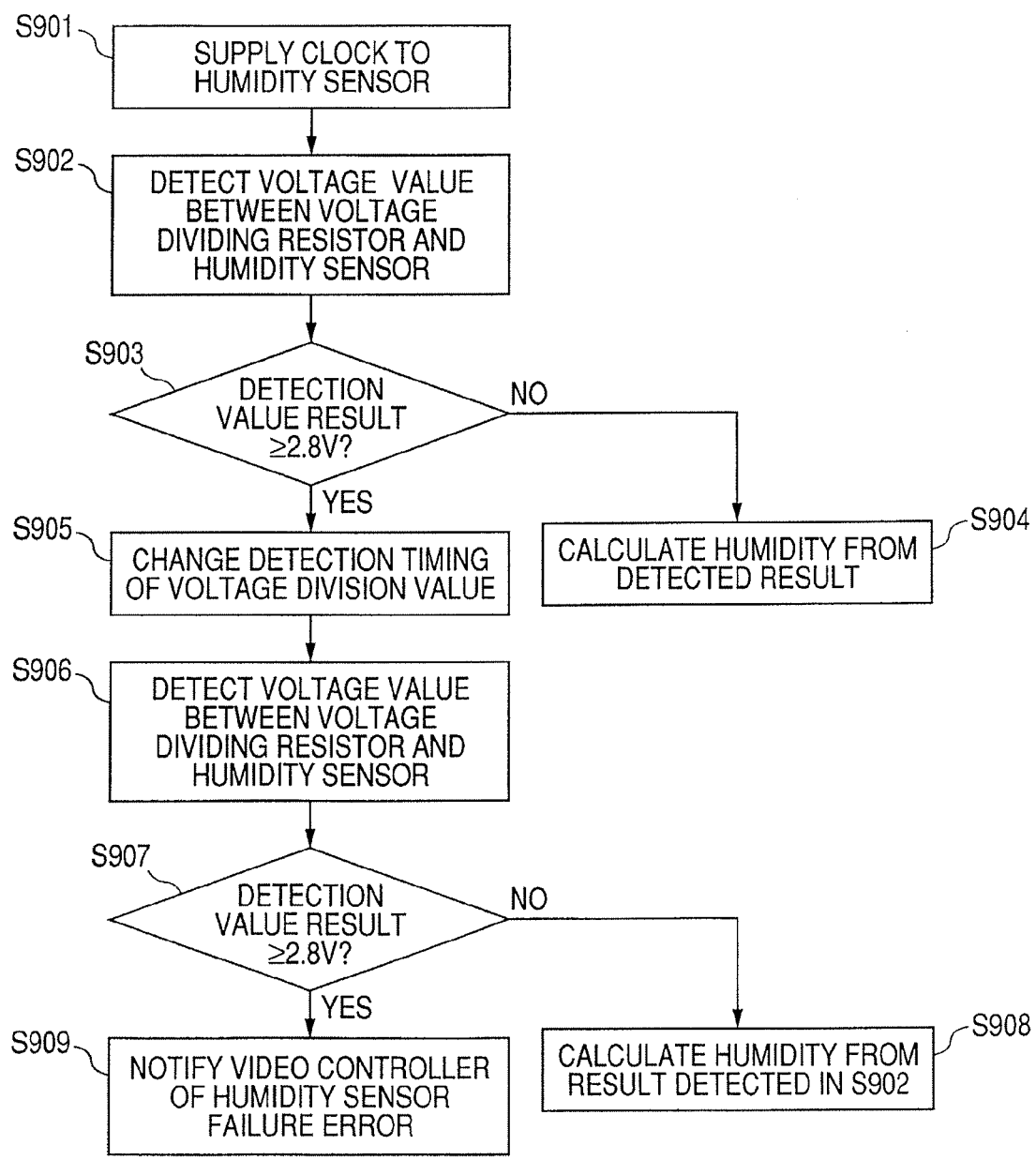
FIG. 9 is a flowchart showing processes of an embodiment 2.
Figure 10:
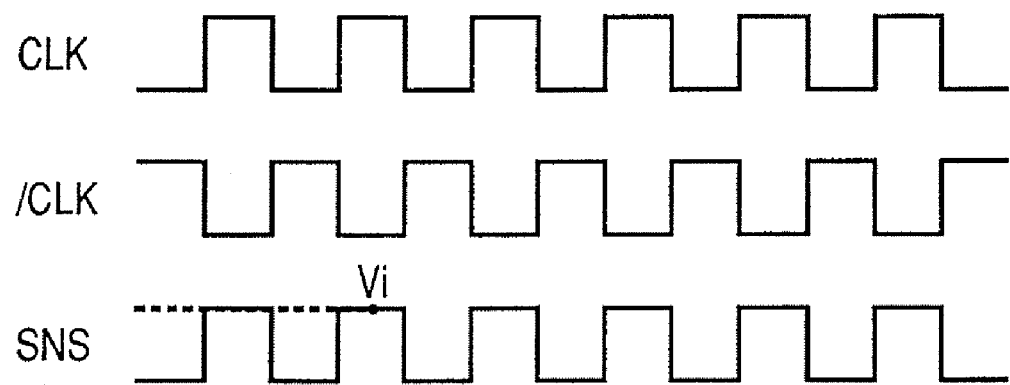
FIG. 10 is a waveform diagram of a humidity detecting circuit.

A flow of the error detection under the low humidity environment will now be described with reference to a flowchart of FIG. 9. In the flowchart, each processing step is abbreviated as "S" and the humidity sensor element is abbreviated as "humidity sensor". The clock signal of the frequency (1 kHz), the amplitude (+3.3V), and the duty ratio (50%) is output from the microprocessor in FIG. 1 (S901). The output clock signal and the signal from the humidity detecting circuit are shown in FIG. 10. The output signal CLK and the output signal /CLK whose polarity is opposite to the polarity of the output signal are supplied to the humidity sensor element 101 through the voltage dividing resistor 102. The value Vi of the voltage division (refer to FIG. 10) with the resistor 102 after the elapse of 250 μsec from the leading edge of the output clock signal CLK is input to the microprocessor (S902). Whether or not a detection result in S902 is equal to or less than 2.8V is discriminated (S903). When it is smaller than 2.8V, the humidity is calculated from the detection result by using the detection voltage–humidity conversion table shown in FIG. 6 (S904).

Figure 11:
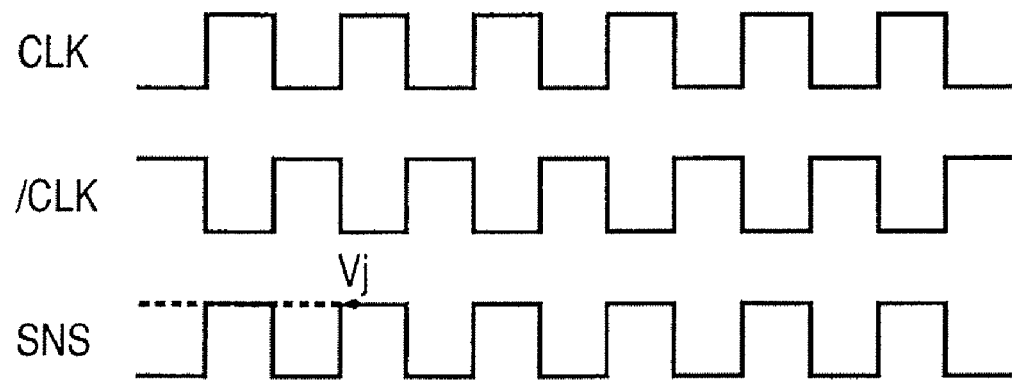
FIG. 11 is a waveform diagram of the humidity detecting circuit.

When the voltage is equal to or larger than 2.8V, it is determined that the humidity is low or the humidity sensor element has failed. The apparatus is shifted to the failure discriminating mode. In the failure discriminating mode, the detection timing for inputting the voltage division value to the microprocessor is changed from the timing after the elapse of 250 μsec from the leading edge of the clock signal CLK to the timing after the elapse of 50 μsec (S905). The output clock signal and the signal from the humidity detecting circuit are shown in FIG. 11. The output signal and the output signal whose polarity is opposite to the polarity of the output signal are supplied to the humidity sensor element 101 through the voltage dividing resistor 102. The value Vj of the voltage division (refer to FIG. 11) with the resistor 102 is input to the microprocessor (S906). Whether or not a detection result in S906 indicates that the voltage division value Vj is equal to or larger than 2.8V is discriminated (S907). If it is smaller than 2.8V, the humidity is calculated by using the detection voltage–humidity conversion table shown in FIG. 6 from the voltage division value Vi which has already been detected (S908). When it is equal to or larger than 2.8V, the engine controller 204 notifies the video controller 203 of the error indicative of the failure of the humidity sensor element (S909).

The reason why the apparatus is shifted to the failure discriminating mode when the voltage is equal to or larger than 2.8V is as follows.

According to the humidity detecting circuit of the embodiment, in the case of the low humidity of 20% or less, a change amount of the detection voltage to a humidity change is small (refer to FIG. 16). Therefore, it is difficult to discriminate the state where the humidity detecting element fails and outputs a predetermined voltage value of 2.8V or more and the state of the low humidity. The apparatus is shifted to the failure discriminating mode in order to discriminate whether or not the humidity sensor element has failed.

An example of specific numerical values of the embodiment is shown below. The clock signal of the frequency (1 kHz), the amplitude (+3.3V), and the duty ratio (50%) is output from the microprocessor in FIG. 1. The output signal CLK and the output signal /CLK whose polarity is opposite to the polarity of the output signal are supplied to the humidity sensor element 101 through the voltage dividing resistor 102. The value of the voltage division with the voltage division resistance of 68 kΩ is input to the microprocessor. When the detection voltage is equal to 3.2V, the apparatus is shifted to the failure discriminating mode. In the failure discriminating mode, the detection timing for inputting the voltage division value to the microprocessor is changed from the timing after the elapse of 250 μsec from the leading edge of the clock signal CLK to the timing after the elapse of 50 μsec. The output signal and the output signal whose polarity is opposite to the polarity of the output signal are supplied to the humidity sensor element through the voltage dividing resistor 102. The value of the voltage division with the voltage division resistance of 68 kΩ is input to the microprocessor. When the detection voltage is equal to 32.V, that is, when it is equal to 3.2V corresponding to the value which is equal to or larger than 2.8V, it is determined that the humidity sensor element has failed. The video controller 203 is notified of the error showing the failure of the humidity sensor element. By using such a method, the abnormality of the humidity sensor element can be discriminated by the reasonable circuit construction. Thus, the images of the high quality can be continuously provided by setting the image forming conditions according to the output of the humidity sensor element.

Embodiment 3

A humidity detecting circuit in the embodiment 3 will now be described. In this embodiment, a failure detection in peripheral circuits around the humidity sensor including the humidity detecting circuit will be described. Since a construction of hardware is similar to that of the embodiment 1, its explanation is also cited in common and a specific description is omitted here.

Figure 12:
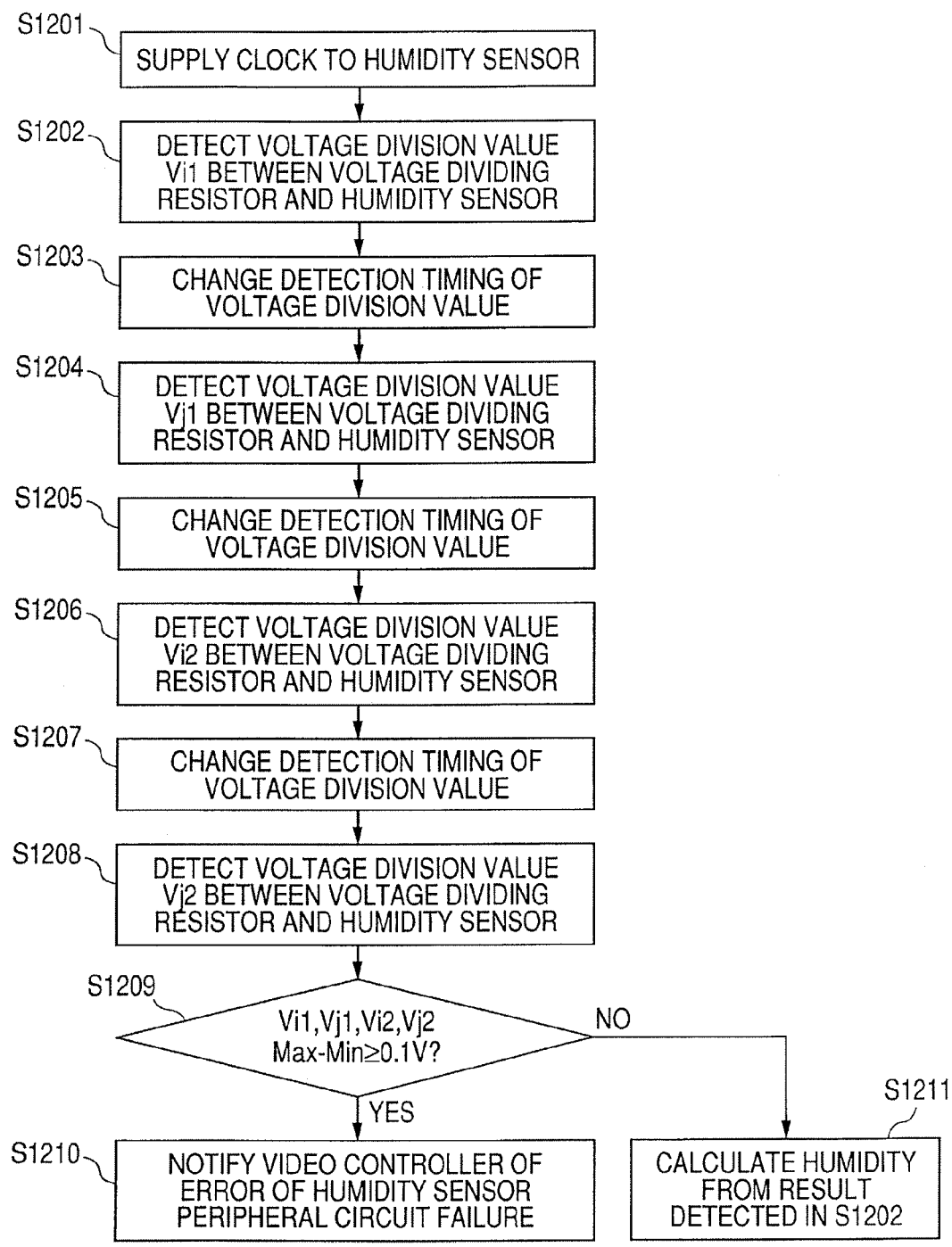
FIG. 12 is a flowchart showing processes of an embodiment 3.
Figure 13:
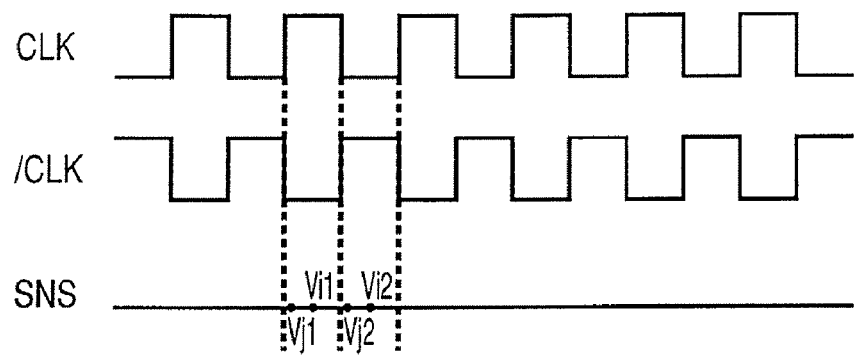
FIG. 13 is a waveform diagram of a humidity detecting circuit.

A flow of processes in the embodiment will now be described with reference to a flowchart of FIG. 12. In the flowchart, each processing step is abbreviated as "S" and the humidity sensor element is abbreviated as "humidity sensor". The clock signal of the frequency (1 kHz), the amplitude (+3.3V), and the duty ratio (50%) is output from the microprocessor in FIG. 1 (S1201). The output clock signal and the signal from the humidity detecting circuit are shown in FIG. 13. The output signal CLK and the output signal /CLK whose polarity is opposite to the polarity of the output signal are supplied to the humidity sensor element 101 through the voltage dividing resistor 102. A value Vi1 of the voltage division (refer to FIG. 13) with the resistor 102 after the elapse of 250 μsec from the leading edge of the output clock signal CLK is input to the microprocessor (S1202). The detection timing for inputting the voltage division value to the microprocessor is changed from the timing after the elapse of 250 μsec from the leading edge of the clock signal CLK to the timing after the elapse of 50 μsec (S1203). The output signal and the output signal whose polarity is opposite to the polarity of the output signal are supplied to the humidity sensor element 101 through the voltage dividing resistor 102. A value Vj1 of the voltage division (refer to FIG. 13) with the resistor 102 is input to the microprocessor (S1204).

The detection timing for inputting the voltage division value to the microprocessor is changed from the timing after the elapse of 50 μsec from the leading edge of the clock signal CLK to the timing after the elapse of 750 μsec (S1205). The output signal and the output signal whose polarity is opposite to the polarity of the output signal are supplied to the humidity sensor element 101 through the voltage dividing resistor 102.

A value Vi2 of the voltage division (refer to FIG. 13) with the resistor 102 is input to the microprocessor (S1206). The detection timing for inputting the voltage division value to the microprocessor is changed from the timing after the elapse of 750 μsec from the leading edge of the clock signal CLK to the timing after the elapse of 550 μsec (S1207). The output signal and the output signal whose polarity is opposite to the polarity of the output signal are supplied to the humidity sensor element 101 through the voltage dividing resistor 102. A value Vj2 of the voltage division (refer to FIG. 13) with the resistor 102 is input to the microprocessor (S1208).

From detection results Vi1, Vi2, Vj1, and Vj2 in S1201 to S1208, whether or not (Max−Min) is equal to or larger than 0.1V is discriminated (S1209). If it is equal to or larger than 0.1V, the engine controller 204 notifies the video controller 203 of an error indicative of the failure of a peripheral circuit of the humidity sensor element (S1210). If it is smaller than 0.1V, the humidity is calculated by using the detection voltage–humidity conversion table shown in FIG. 6 from the voltage division value Vi1 detected in step S1202 (S1211).

That is, a plurality of detection timing is set. When the value of a difference between the maximum value and the minimum value among a plurality of detected voltages is large (equal to or larger than 0.1V), it is determined that the circuit has failed.

An example of specific numerical values of the embodiment is shown below. The clock signal of the frequency (1 kHz), the amplitude (+3.3V), and the duty ratio (50%) is output from the microprocessor in FIG. 1. The output signal CLK and the output signal /CLK whose polarity is opposite to the polarity of the output signal are supplied to the humidity sensor element 101 through the voltage dividing resistor 102. As for the detection timing for inputting the voltage division value to the microprocessor, the value Vi1=1.2V of the voltage division with the voltage division resistance of 68 kΩ is input to the microprocessor after the elapse of 250 μsec from the leading edge of the clock signal. The detection timing for inputting the voltage division value to the microprocessor is changed from the timing after the elapse of 250 μsec from the leading edge of the clock signal CLK to the timing after the elapse of 50 μsec. The value Vj1=1.2V of the voltage division with the voltage division resistance of 68 kΩ is input to the microprocessor. The detection timing for inputting the voltage division value to the microprocessor is changed from the timing after the elapse of 50 μsec from the leading edge of the clock signal CLK to the timing after the elapse of 750 μsec. The value Vi2=1.2V of the voltage division with the voltage division resistance of 68 kΩ is input to the microprocessor. The detection timing for inputting the voltage division value to the microprocessor is changed from the timing after the elapse of 750 μsec from the leading edge of the clock signal CLK to the timing after the elapse of 550 μsec. The value Vj2=1.2V of the voltage division with the voltage division resistance of 68 kΩ is input to the microprocessor. Among Vi1, Vj1, Vi2, and Vj2, since (Max−Min)=0V and does not exceed 0.1V, the error showing the failure of the peripheral circuit around the humidity sensor is not notified. When it exceeds 0.1V, the error showing the failure of the peripheral circuit around the humidity sensor is notified.

By using such a method, the abnormality of the peripheral circuit around the humidity sensor can be discriminated by the simple circuit construction. The images of the high quality can be continuously provided by setting the image forming conditions according to the output of the humidity sensor element.

In each of the above embodiments, the error is discriminated by checking whether or not the output waveform of the sensor signal SNS is normal by changing the detection timing. Since the waveform of the sensor signal SNS changes depending on the circuit construction, the detection timing is properly changed to the optimum value according to the circuit construction.

Although the voltage is detected at the timing after the elapse of the predetermined time from the rising (leading edge) of the clock signal (CLK) in each of the above embodiments, the falling (trailing edge) may be used as a reference.

Figure 14:
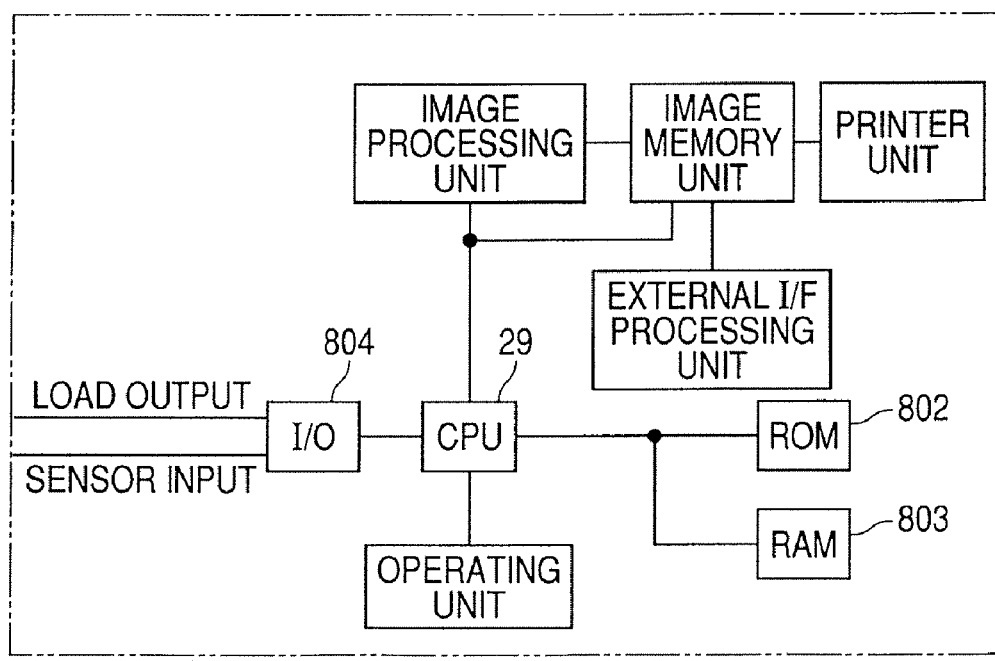
FIG. 14 is a diagram illustrating a schematic construction of a control system.
Figure 15:
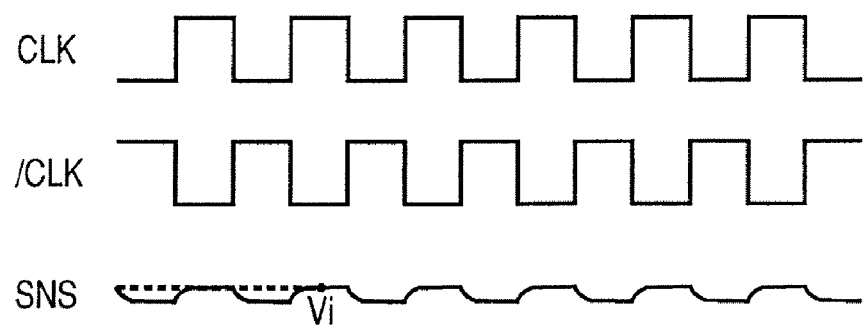
FIG. 15 is a waveform diagram of a humidity detecting circuit in the related art.

FIG. 14 illustrates a schematic construction of a control system in each of the above embodiments. The control system has a CPU 29, a ROM 802 in which a control program has been written, and a RAM 803 for providing a work area for the CPU 29 to execute various processes (corresponding to the microprocessor in FIG. 1). The control system controls the image forming operation and executes the processes shown in the flowcharts. Description of other portions in FIG. 14 is omitted here.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-039125, filed Feb. 16, 2006 which is hereby incorporated by reference herein in its entirety.

What is claimed is:

1. A humidity measuring apparatus comprising:
 a humidity detecting element whose resistance value changes according to a humidity change;
 a resistor serially connected to the humidity detecting element;
 a signal output unit which outputs a clock signal to the humidity detecting element and the resistor; and
 a measuring unit which detects a voltage at a connecting point of the humidity detecting element and the resistor at a predetermined timing from one of a leading edge and a trailing edge of the clock signal so as to determine a humidity, and which detects a voltage at the connecting point at a timing different from the predetermined timing so as to determine an abnormality of the humidity detecting element.

2. An apparatus according to claim 1, further comprising a discriminating unit which discriminates whether or not the humidity detecting element is abnormal based on the voltage detected at the timing different from the predetermined timing.

3. An apparatus according to claim 1, wherein the measuring unit detects a plurality of voltages of the connecting point at a plurality of timing different from the predetermined timing so as to determine the abnormality of the humidity detecting element.

4. An apparatus according to claim 2, wherein if it is determined by the discriminating unit that the humidity detecting element is abnormal, the discriminating unit outputs and error.

5. An apparatus according to claim 3, wherein the abnormality of the humidity detecting element is detected based on a maximum value and a minimum value among the plurality of detected voltages.

6. An image forming apparatus comprising:
 an image forming unit which forms an image;
 a humidity detecting apparatus having a humidity detecting element whose resistance value changes according to a humidity change and a resistor serially connected to the humidity detecting element;

a signal output unit which outputs a clock signal to the humidity detecting element and the resistor;

a control unit which controls an image forming condition of the image forming unit based on an output from the humidity detecting apparatus, a measuring unit which detects a voltage at a connecting point of the humidity detecting element and the resistor at predetermined timing from one of a leading edge and a trailing edge of the clock signal so as to determine a humidity, and which detects a voltage at the connecting point at timing different from the predetermined timing so as to determine the abnormality of the humidity detecting element.

7. An apparatus according to claim 6, further comprising a discriminating unit which discriminates whether or not there is an abnormality of the humidity detecting element based on the voltage detected at the timing different from the predetermined timing.

8. An apparatus according to claim 6, wherein the measuring unit detects a plurality of voltages of the connecting point at a plurality of timing different from the predetermined timing so as to determine the abnormality of the humidity detecting element.

9. An apparatus according to claim 7, wherein if it is determined by the discriminating unit that the humidity detecting element is abnormal, the discriminating unit outputs an error to the control unit.

10. An apparatus according to claim 8, wherein the abnormality of the humidity detecting element is detected based on a maximum value and a minimum value among the plurality of detected voltages.

* * * * *